United States Patent [19]

Meguro et al.

[11] Patent Number: 4,789,675

[45] Date of Patent: Dec. 6, 1988

[54] 1,4-BENZOXAZINE DERIVATIVES AND PHARMACEUTICAL USE

[75] Inventors: Kanji Meguro, Nishinomiya; Kohei Nishikawa, Kyoto, both of Japan

[73] Assignee: Takeda Chemical Industries, Ltd., Osaka, Japan

[21] Appl. No.: 13,441

[22] Filed: Feb. 10, 1987

[30] Foreign Application Priority Data

Feb. 11, 1986 [JP] Japan .................................. 61-28720
Apr. 15, 1986 [JP] Japan .................................. 61-87503

[51] Int. Cl.$^4$ .................. A61K 31/535; C07D 413/06
[52] U.S. Cl. .............................. 514/229.8; 514/230.5; 544/101; 544/105
[58] Field of Search ................ 544/101, 105; 514/227, 514/229, 234, 236, 237, 239, 230.5, 229.8

[56] References Cited

U.S. PATENT DOCUMENTS

| | | | |
|---|---|---|---|
| 3,401,166 | 9/1968 | Krapcho | 544/105 X |
| 4,640,916 | 2/1987 | Meguro et al. | 514/224.2 |
| 4,704,390 | 11/1987 | Caprathe et al. | 514/231 |

FOREIGN PATENT DOCUMENTS

| | | |
|---|---|---|
| 0154969 | 9/1985 | European Pat. Off. . |
| 0171702 | 2/1986 | European Pat. Off. . |
| 2080791 | 2/1982 | United Kingdom . |

*Primary Examiner*—Richard L. Raymond
*Attorney, Agent, or Firm*—Wenderoth, Lind & Ponack

[57] ABSTRACT 1,4-Benzoxazine derivatives representable by the general formula;

wherein
$R^1$ and $R^2$ independently stand for hydrogen, halogen atom, nitro group, an optionally substituted lower alkyl group, an optionally substituted amino group, an optionally substituted hydroxyl group, a lower alkoxycarbonyl group, or when $R^1$ and $R^2$ are adjacent to each other,
$R^1$ and $R^2$ combinedly stand for a ring representable by —CH$_2$)$_m$ (wherein m denotes an integer of 3 to 5) or —O—CH$_2$)$_n$O— (wherein n denotes an integer of 1 to 3),
$R^3$ stands for hydrogen or a lower alkyl group,
$R^4$ and $R^5$ independently stand for hydrogen, halogen atom, an optionally substituted lower alkyl group or an optionally substituted hydroxyl group, and
A stands for an alkylene group or acid addition salts thereof, are useful as prophylactic or therapeutic drugs for, among others, hypertension or ischemic dieases.

19 Claims, No Drawings

1,4-BENZOXAZINE DERIVATIVES AND PHARMACEUTICAL USE

This invention relates to novel 1,4-benzoxazine derivatives having excellent pharmacological activity, a method of preparing same and pharmaceutical compositions containing same. The compounds of this invention have a strong hypotensive activity, vasodilating activity, etc., thus being useful as, among other, pharmaceuticals.

A number of compounds having 2H-1,4-benzoxazin-3(4H)-one as the skeletal structure have so far been synthesized.

In the specification of Toku-Kai (Japanese patent application laid-open) Sho No. 49-125,529, compounds showing anti-fungal action; in European Journal of Medicinal Chemistry Vol. 10, pp. 37 (1975), those showing analgesic action; in Journal of Medicinal Chemistry Vol. 20, pp. 729 (1977), those showing central nervous system controlling action; in the specification of German patent application laid-open No. 2,653,810, those showing anti-inflammatory action; in the specification of U.S. Pat. No. 3,557,103, those showing anti-arrhythmia action; and in Pharmazie Vol. 38, pp. 885 (1983), those showing herbicidal action are disclosed, respectively. These compounds, however, are all limited to those having, at the 2-position, e.g. alkyl, phenyl, benzyl, benzylidene or phenylimino, and only a few compounds having aminoalkyl group at the 2-position have been reported. Namely, excepting the disclosure of 2-phenyl-2-aminoalkyl-1H-1,4-benzoxazin-3(4H)-ones as tranqulizers in the specification of U.S. Pat. No. 3,401,166, only in Journal of Pharmaceutical Society of Japan, Vol. 97, p. 1039 (1977), disclosure on anti-tumor action of 2-(2-morpholinoethyl)- and 2-[2-(phenylamino)ethyl]-2H-1,4-benzoxazin-3(4H)-one is disclosed.

3-Oxo-1,4-benzoxazine derivatives have many fields to be explored on their utilization, but, especially as to compounds having at the 2-position phenylpiperazinylalkyl group and their pharmacological actions, nothing has been known at all. This invention is to provide novel 1,4-enzoxazine derivatives having excellent pharmacological activities.

This invention relates to compounds representable by the general formula;

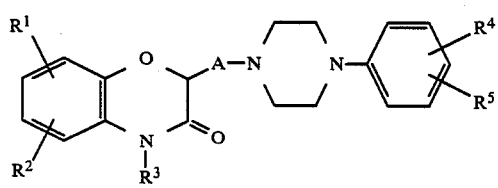

wherein
R$^1$ and R$^2$ independently stand for hydrogen, halogen atom, nitro group, an optionally substituted lower alkyl group, an optionally substituted amino group, an optionally substituted hydroxyl group, a lower alkoxycarbonyl group, or
when R$^1$ and R$^2$ are adjacent to each other,
R$^1$ and R$^2$ combinedly stand for a ring representable by
-(CH$_2$)$_m$- (wherein m denotes an integer of 3 to 5) or —O-(CH$_2$)$_n$O— (wherein n denotes an integer of 1 to 3),
R$^3$ stands for hydrogen or a lower alkyl group,
R$^4$ and R$^5$ independently stand for hydrogen, halogen atom, an optionally substituted lower alkyl group or an optionally substituted hydroxyl group, and
A stands for an alkylene group
or an acid addition salt thereof, a method of preparing them and pharmaceutical compositions containing them.

In the above-mentioned formula (I), halogens representable by R$^1$, R$^2$, R$^4$ and R$^5$ are exemplified by fluorine, chlorine, bromine and iodine, especially fluorine and chlorine being preferable, and at least one of R$^4$ and R$^5$ being preferably fluorine.

Optionally substituted lower alkyl groups representable by R$^1$, R$^2$, R$^4$ and R$^5$ are preferably those having 1 to 6 carbon atoms, which are exemplified by methyl, ethyl, propyl, isopropyl, butyl, isobutyl, sec-butyl, tert-butyl, pentyl, isopentyl, neopentyl, hexyl groups as well as those having a suitable substituent or substituents. As the substituents of those lower alkyl groups are mentioned for example halogen atoms (e.g. fluorine, chlorine, bromine or iodine), hydroxyl group, a lower alkoxy group, and the number of substituents being preferably 1 to 3. Lower alkyl groups having substituents mentioned as above are exemplified by trifluoromethyl group, trifluoroethyl group, difluoromethyl group, trichloromethyl group, hydroxymethyl group, 1-hydroxyethyl group, 2-hydroxyethyl group, methoxymethyl group, ethoxymethyl group, 1-methoxyethyl group, 2-methoxyethyl group, 2-ethoxymethyl group, 2,2-dimethoxyethyl group, 2,2-diethoxyethyl group, etc.

Optionally substituted amino groups representable by R$^1$ and R$^2$ are exemplified by amino group and the amino group having appropriate substituents, especially those usable as groups for protecting the amino group, such as mono- or bis($\beta$-hydroxyethyl)amino group, monoacylamino group, or di-lower alkylamino group, sulfonylamino group, etc.

The mono- or di-lower alkylamino groups are exemplified by mono- or di-substituted amino groups with alkyl groups having 1 to 4 carbon atoms, such as methylamino, ethylamino, n-propylamino, isopropylamino, n-butylaiino, dimethylamino, diethylamino, di-npropylamino, methyl-ethylamino, etc.

The acylamino group is exemplified by alkanoylamino groups having 2 to 4 carbon atoms (e.g. acetylamino propionylamino, n-butyrylamino, iso-butyryl-amino group, etc.).

The sulfonylamino group is exemplified by alkylsulfonylamino groups having 1 to 4 carbon atoms (e.g. methylsulfonylamino, ethylsulfonylamino group, etc.).

Optionally substituted hydroxyl groups representable by R$^1$, R$^2$, R$^4$ and R$^5$ are exemplified by hydroxyl group and the hydroxyl group having appropriate substituents, especially those usable as groups for protecting the hydroxyl group, such as alkoxy group, aralkyloxy group, acyloxy group, etc.

The alkoxy group is preferably a lower alkoxy group whose carbon number is 1 to 6 (e.g. methoxy, ethoxy, propoxy, isopropoxy, butoxy, isobutoxy, secbutoxy, tert-butoxy, pentoxy, isopentoxy, neopentoxy, hexyloxy group).

The aralkyloxy group is exemplified by phenyl-C$_{1-4}$alkyloxy group (e.g. benzyloxy, phenethyloxy group, etc.).

The acyloxy group is preferably alkanoyloxy group having 2 to 4 carbon atoms (e.g. acetyloxy, propionyloxy, n-butyryloxy, iso-butyryloxy, etc.).

The substituted hydroxyl groups of $R^4$ and $R^5$ include the case where $R^4$ and $R^5$ combinedly form methylenedioxy group.

Lower alkoxycarbonyl groups represented by $R^1$ and $R^2$ are exemplified by those formed by combination of a carbonyl group and an alkoxy group having 1 to 6 carbon atoms as described in reference to $R^1$, $R^2$, $R^4$ and $R^5$.

When $R^1$ and $R^2$ are adjacent to each other, $R^1$ and $R^2$ may be combined to form a ring shown by $-(CH_2)_m-$ or $-O-(CH_2)_nO-$, and the ring includes 5 to 7-membered ring formed together with carbon atoms on the benzene rings. Among these rings, 5 to 6-membered rings where m is 3 or 4 and 5 to 6-membered rings where n is 1 or 2 are preferable, and further preferable are those condensed at 6,7-position of the 1,4-benzoxazine skeleton.

As the lower alkyl group represented by $R^3$, preferable are those having 1 to 6 carbon atoms described in reference to the above $R^1$, $R^2$, $R^4$ and $R^5$.

As the alkylene group represented by A are preferable straight-chain or branched ones having 2 to 5 carbon atoms, as exemplified by ethylene, propylene, trimethylene, 1-methyltrimethylene, 2-methyltrimethylene, 3-methyltrimethylene, tetramethylene, pentamethylene, etc., especially trimethylene being preferable.

The compound of the above formula (I) has basic nitrogen atoms, which is capable of forming salts with pharmacologically acceptable inorganic or organic acids. These acids are inorganic ones as exemplified by hydrochloric acid, hydrobromic acid, sulfuric acid, phosphoric acid, etc., and organic ones as exemplified by acetic acid, malonic acid, maleic acid, fumaric acid, malic acid, tartaric acid, citric acid, methanesulfonic acid, benzenesulfonic acid, toluenesulfonic acid, etc.

The compound of the formula (I) which has an asymmetric carbon, can exist as a mirror image isomer or a diastereomer, and can be resolved into a pure isomer upon necessity. A mixture of diastereomers can be separated by a conventional means such as fractional recrystallization using a suitable solvent or chromatography using for example silica gel. In case of racemic compounds, they can likewise be resolved into the respective mirror image isomers by conventional means, for example, allowing them to form salts with an optically active acid (e.g. tartaric acid, dibenzoyl tartaric acid, N-acetylphenylalanine, camphor sulfonic acid, 1,1′-binaphthyl-2,2′-diyl hydrogenphosphate, etc.), then conducting selective crystallization or fractional recrystallization, followed by neutralizing them with a suitable base (e.g. sodium hydroxide, potassium hydroxide, sodium carbonate, potassium carbonate, sodium hydrogencarbonate, potassium hydrogencarbonate, ammonia, etc.) to lead to the free bases.

This invention also relates to a method of preparing compounds of the formula (I). Compounds of the formula (I) can be prepared by for example the following methods.

Method A:

A compound representable by the formula (II);

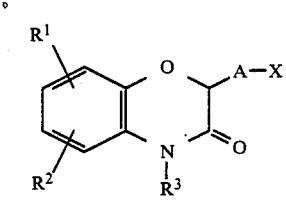

wherein $R^1$, $R^2$, $R^3$ and A are of the same meaning as defined above, and

X stands for a leaving group is allowed to react with a compound representable by the general formula (III);

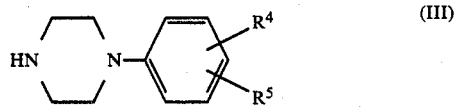

wherein $R^4$ and $R^5$ are of the same meaning as defined above.

Method B:

A compound representable by the formula (IV);

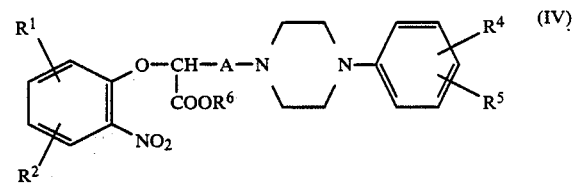

wherein $R^1$, $R^2$, $R^4$, $R^5$ and A are of the same meaning as defined above, and $R^6$ stands for, like $R^3$, hydrogen or a lower alkyl group is subjected to reduction, then to ring closure reaction, followed by, upon necessity, alkylation.

Method C:

A compound representable by the formula (V);

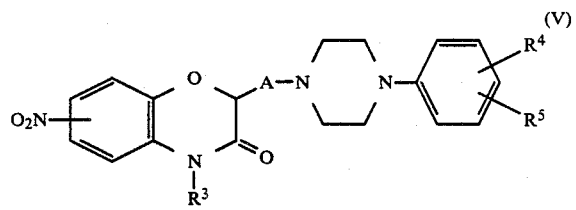

wherein $R^3$, $R^4$, $R^5$ and A are of the same meaning as defined above is subjected to reduction, followed by, if necessary, acylation or sulfonylation to thereby prepare a compound representable by the formula (VI);

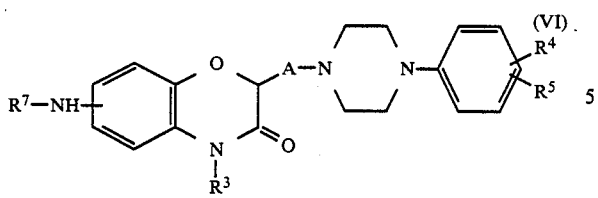

wherein
R³, R⁴, R⁵ and A are of the same meaning as defined above, and
R⁷ stands for hydrogen, acyl group or sulfonyl group.

In the above-mentioned formula (II), the leaving group represented by X is exemplified by halogen (e.g. chlorine, bromine, iodine, etc.), alkylsulfonyloxy group (e.g. methylsulfonyloxy, ethylsulfonyloxy, etc.), arylsulfonyloxy group (e.g. phenylsulfonyloxy, tolylsulfonyloxy, etc.), etc. In the formula (IV), the lower alkyl group represented by R⁶ is exemplified by those similar to the groups set forth in reference to the afore-mentioned R¹ to R⁵. The acyl group and sulfonyl group represented by R⁷ are respectively exemplified by the acyl group and sulfonyl group corresponding to the acylamino group and sulfonylamino group mentioned in R¹, R², R⁴ and R⁵. The following is a brief explanation of the respective methods.

Method A:

This method can be conducted by heating the compounds (II) and (III) in the presence or absence of an appropriate solvent. The solvent is exemplified by alcohols such as methanol, ethanol, propanol, 2-propanol, butanol, 2-methoxyethanol, etc., ethers such as dioxane, tetrahydrofuran, dimethoxyethane, etc., aromatic hydrocarbons such as benzene, toluene, xylene, etc., ethyl acetate, acetonitrile, pyridine, N,N-dimethylformamide, dimethylsulfoxide, etc., or a suitable mixture thereof. As an acid (HX) attributable to the leaving group X is produced in this reaction, the reaction can be conducted in the presence of a suitable acid acceptor, e.g. sodium carbonate, potassium carbonate, triethylamine, N-methylmorpholine, etc., or the reaction is allowed to proceed by adding an excess amount of (III) which is allowed to act also as an acid acceptor. The amount of (III) is usually 1 to 3 mole relative to 1 mole of (II), and the amount of an acid acceptor is preferably about 1 to 3 mole relative to 1 mole of (II). The reaction temperature ranges, in any case, from about 20° C., to about 200° C., preferably from about 50° C. to about 150° C.

Method B:

In this method, the nitro group of a compound (IV) is reduced, then cyclized, followed by, if necessary, alkylation to produce the object compound (I). This reduction reaction can be conducted by catalytic eduction or a conventional means such as one using a metal and an acid. The catalytic reduction can be conducted usually at room temperature under normal pressure using a catalyst such as Raney nickel, palladium carbon, palladium black, platinum oxide, etc. in a solvent (e.g. methanol, ethanol, ethyl acetate, dioxane, tetrahydrofuran, acetic acid, etc.), and, when necessary, in the presence of an acid (e.g. hydrochloric acid, hydrobromic acid, acetic acid, etc.) in an amount necessary for neutralizing the basicity of (IV). For accelerating the reaction, the reaction can be conducted under suitably elevated pressure or/and elevated temperature. Examples of the metal and acid are zinc-acetic acid, iron-acetic acid, iron-hydrochloric acid tin-hydrochloric acid, etc., and the reaction is conducted usually at temperatures of about 40° C. to about 150° C. In this reduction reaction, at first a compound representable by the formula (VII);

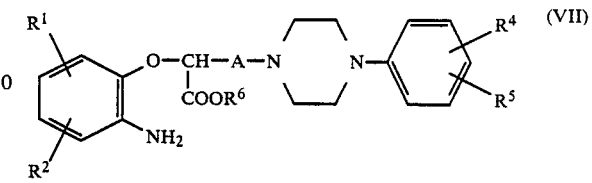

wherein
the symbols in the formula are of the same meaning as defined above
is produced, which is then subjected to cyclization to give a compound of the formula (I');

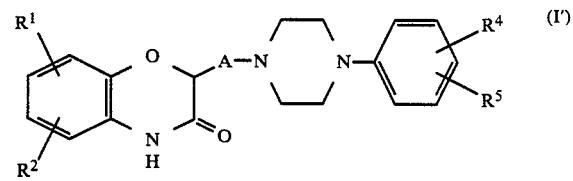

wherein the symbols in the formula are of the same meaning as defined above.

When this cyclization reaction proceeds relatively slowly under the conditions employed for the reduction of (IV), the reaction can be accelerated by suitably heating (about 80° to about 150° C.) or by heating (about 50° to about 120° C.) together with an acid (e.g. hydrochloric acid, hydrobromic acid, p-toluenesulfonic acid, acetic acid, etc.). In case of conducting this cyclization reaction, the reaction solution employed for the reduction can be used as it is, or, (VII) or a mixture of (VII) and (I'), after being separated from the reaction solution, can be subjected to cyclization reaction.

By the above method, the object compound (I) wherein R is hydrogen, i.e. (I'), is produced, which is then subjected, when necessary, to alkylation, to thereby obtain the object compound (I) wherein R is a lower alkyl. This alkylation reaction can be conducted by using an alkylating agent in an organic solvent in the presence of a base. The base varies with kinds of the solvent then employed, which is exemplified by alcohols such as methanol, ethanol, etc., ethers such as tetrahydrofuran, dioxane, dimethoxyethane, diethylether, etc., N,N-dimethylformamide, dimethylsulfoxide, etc. The base is exemplified by sodium methoxide, sodium ethoxide, potassium t-butoxide, sodium hydride, potassium hydride, sodium amide, etc. The alkylating agent is exemplified by alkyl halide (e.g. chloride, bromide, iodide, etc.), dialkylsulfate, alkylsulfonate (e.g. methanesulfonate, ethanesulfonate, benzenesulfonate, toluenesulfonate, etc.), etc. In this reaction, it is preferable to allow a compound (I') to react with a base in a solvent to form an anion, then to allow an alkylating agent to act thereon. The reaction temperature is usually in the range of about −10° C. to about 100° C., preferably about 0° C. to about 40° C.

Method C:

The compound (I) wherein R¹ or R² stands for amino group, acylamino group or sulfonylamino group [i.e. a compound representable by the formula (VI)] can be produced by subjecting a compound (I) wherein $R^1$ or $R^2$ stands for nitro group [i.e. a compound representable by the formula (V)] to reduction, followed by, upon necessity, subjecting the resultant to acylation or sulfonylation. Reduction of the compound (V) can be conducted in exactly the same manner as that of the above-mentioned reduction of the compound (IV). Acylation or sulfonylation of the reduced product can be conducted by using a conventional acylating agent or sulfonylating agent (e.g. acid anhydride, acid halide, sulfonyl halide, etc.) at a temperature range of about 0° C. to about 120° C., when necessary, in the presence of a solvent and a base. The base is exemplified by pyridine, triethylamine, sodium hydroxide, potassium hydroxide, sodium carbonate, potassium carbonate, sodium hydrgencarbonate, potassium hydrogencarbonate, etc. The solvent is exemplified by chloroform, dichloromethane, tetrahydrofuran, dioxane, dimethylformamide, pyridine, acetic acid, etc. If the reduction of (V) is conducted in the presence of an acid anhydride, reduction and acylation can be conducted simultaneously.

When optically active starting compounds (II), (IV) and (V) are employed in the above mentioned Method A to C, optically active object compounds (I) can be produced.

The novel 1,4-benzoxazine derivatives (I) as well as salts thereof thus produced have hypotensive activity, cerebral circulation ameliorating activity, etc. in mammals (e.g. rat, rabbit, dog, cat, man, etc.) due to their vasodilating activity, adrenergic α-receptor-blocking activity, intracellular calcium antagonism, etc. Especially, it is a great characteristic feature of the compounds of this invention that they display intracellular calcium antagonism. Contraction of smooth muscle requires calcium ion ($Ca^{++}$), and this $Ca^{++}$ includes (1) one that influxes into cells through so-called $Ca^{++}$ channel, (2) one that is liberated from the intracellular $Ca^{++}$ store site and (3) one that influxes into cells through the receptor-operated channel. A $Ca^{++}$ channel blocker such as nifedipine hardly acts on (2) and (3). As the compounds acting on (2) and showing antagonism against intracellular $Ca^{++}$, there have been known e.g. trifluoperazine, TMB-8 and W-7, but the latter two compounds are weak in action and do not display antihypertensive action in vivo. Trifluoperazine has not been practically used as an antihypertensive agent or a ameliorant of cerebral circulation, due to its side effects e.g. on the central nervous system. The compounds of this invention having a remarkable intracellular $Ca^{++}$ antagonistic activity are capable of inhibiting contraction caused by any of (1), (2) and (3) mentioned above, and display pharmacological activities in a broader area than conventional $Ca^{++}$ channel blockers. Besides vasodilating action, they also show bronchodilating action, and are expected to be of use as an antiasthmatic drug. The compounds of this invention also have protective action on the damages of ischemic heart, brain and kidney. They have low toxicity and less side effects including orthostatic hypotension often observed by administration of prazosin, one of the typical α-adrenoceptor blockers, and thus are very useful as prophylactics and therapeutic drug against, among others, hypertension, ischemic diseases of e.g. heart, brain and kidney (e.g. cerebral infarction, transient cerebral ischemic attack, myocardial infarction, acute renal failure, nephritis, etc.).

In the use of the compound (I) or its salt as the above-mentioned pharmaceuticals, it can be administered orally or parenterally in such dosage forms as powders, granules, tablets, capsules, injections, etc. which may be prepared by mixing with a pharmaceutically acceptable carrier, excipient or diluent. Although the dosage should vary with such factors as the route of administration, the symptom of patients, and the body weight or the age of patients, 0.05 to 10 mg/kg body weight/day, preferably 0.1 to 5 mg/kg body weight/day, for instance, is orally administered divided into 1 to several times a day, to an adult patient with hypertension.

The starting compounds (II) and (IV) can be prepared by, for example, the following processes as shown in D to H.

Method D

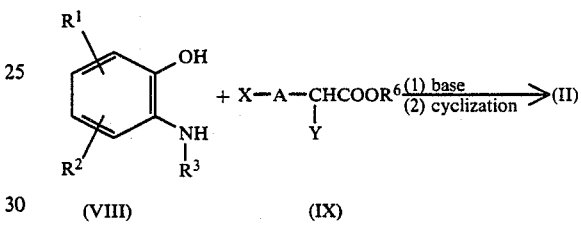

wherein Y stands for halogen atom, and other symbols are of the same meaning as defined above Method E

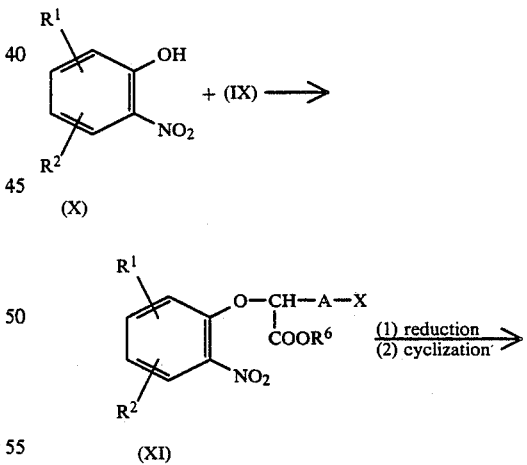

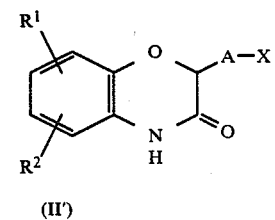

wherein symbols are of the same meaning as defined above

Method F

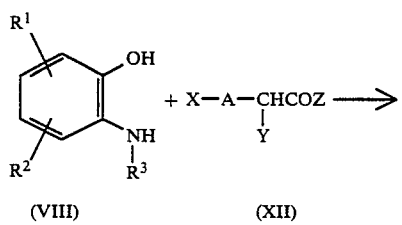

(VIII)       (XII)

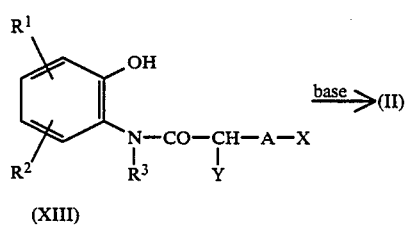

(XIII)

wherein Z stands for halogen atom, and other symbols are of the same meaning as defined above Method G

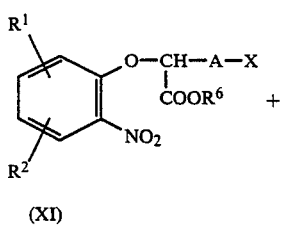

(XI)

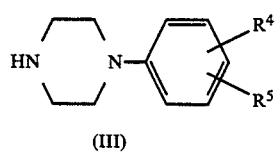

(III)

wherein symbols are of the same meaning as defined above

Method H

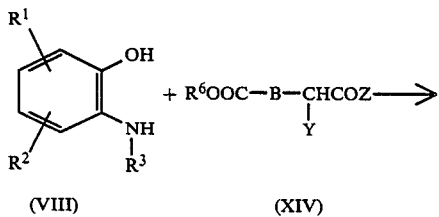

(VIII)       (XIV)

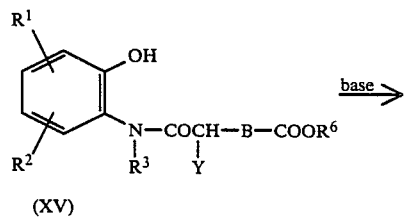

(XV)

-continued
Method H

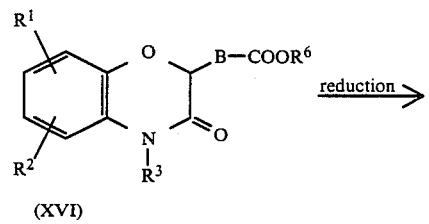

(XVI)

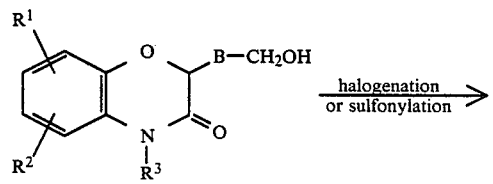

(XVII)

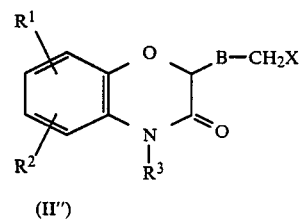

(II″)

wherein B stands for a single bond or an alkylene group, and other symbols are of the same meaning as defined above.

In the above formulae, halogen atoms shown by Y and Z are exemplified by chlorine, bromine, etc. The symbol B represents a single bond or an alkylene whose carbon number is always less than that of A by one, and —B—CH$_2$— is necessarily equivalent to —A—.

The following is a brief description of the afore-mentioned methods.

Method D:

According to this method, a compound (II) can be produced in one step by allowing a compound (VIII) to react with a compound (IX). The reaction can be usually conducted in a suitable solvent at about 0° C. to about 100° C. in the presence of a base. The solvent is exemplified by alkanols such as methanol, ethanol, propanol, 2-propanol, etc., ketones such as acetone, methylethylketone, etc., ethers such as tetrahydrofuran, dioxane, dimethoxyethane, etc., and acetonitrile, dimethylformamide, etc. The base is exemplified by potassium carbonate, sodium carbonate, etc. In this reaction, a compound representable by the formula (XVIII);

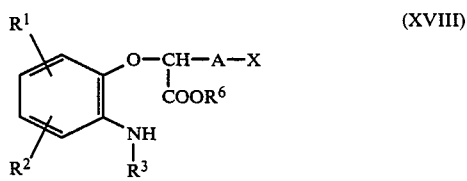

(XVIII)

wherein symbols are of the same meaning as defined above is first produced, which is then cyclized to give (II). When cyclization from (XVIII) to (II) is insufficient, it can be accelerated, in a manner similar to the case of (VII) above, by suitably heating or heating in the presence of an acid such as hydrochloric acid, hydrobromic acid, p-toluenesulfonic acid, acetic acid, etc.

Method E:

In this method, a compound (X) is allowed to react with a compound (IX) to give a compound (XI), which is then reduced and cyclized to produce a compound (II'). The reaction between (X) and (IX) can be conducted in completely the same manner as that of the above-mentioned reaction between (VIII) and (IX). The thus obtained (XI) is then subjected to reduction and cyclization to produce (II'). This reduction reaction can be conducted under completely the same conditions as those described in the Method B of producing the object compound (I) in the foregoing. When the cyclization of the resultant intermediate, a compound of the formula (XVIII');

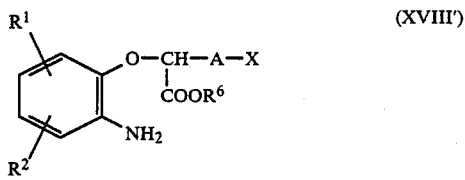

wherein symbols are of the same meaning as defined above is slow, similar treatment to that in the case of (VII) or (XVIII) can be applied to accelerate the reaction to yield (II').

Method F:

In this method, firstly, a compound (VIII) is allowed to react with a compound (XII) to give an N-acyl compound (XIII), which is then cyclized to give a compound (II). This reaction is conducted in a suitable solvent in the presence of a base. As the solvent, use is made of, for example, chloroform, dichloromethane, ethyl acetate, ether, tetrahydrofuran, dioxane, dimethoxyethane, dimethylformamide and a mixture solvent thereof with water. The reaction can be conducted in homogeneous or heterogeneous system. As the base, use is made of, for example, sodium hydrogencarbonae, potassium hydrogencarbonate, sodium carbonate, pyridine, triethylamine, etc. This reaction is usually conducted at about $-10°$ C. to about 50° C., preferably at about 0° C. to about 30° C.

Then, the resultant compound (XIII) is subjected to ring closure reaction in the presence of a base to produce a compound (II). This reaction can also be conducted in a solvent, like in the above-mentioned reaction between (VIII) and (XII), in the presence of a base, for example, sodium carbonate, potassium carbonate, sodium acetate, potassium acetate, etc. at about 0° C. to about 100° C., preferably at about 15° C. to about 40° C. In the reaction between (VIII) and (XII), when a base such as sodium carbonate, potassium carbonate, etc., is used, the resultant compound (XIII) is, depending on conditions, further cyclized to give a compound (II).

Method G:

In this method, a compound (XI) is allowed to react with a compound (III) to produce a compound (IV). This reaction can be conducted in completely the same manner as that of the reaction between a compound (II) and a compound (III) in Method A.

Method H:

In this method, a compound (VIII) is first allowed to react with a compound (XIV) to yield an N-acyl compound (XV), which is then cyclized to (XVI). These reactions are conducted in the same manner as in the reaction of (VIII) with (XII) followed by cyclization to yield (II) shown in Method F. Then the compound (XVI) thus produced is reduced to (XVII). This reduction is preferably carried out by the use of e.g. sodium borohydride in a solvent such as methanol, ethanol, a mixture of methanol or ethanol and tetrahydrofuran or dioxane, etc., or lithium alminum hydride in a solvent such as ethyl ether, tetrahydrofuran, dioxane, dimethoxyethane, etc. Reaction temperature ranges from about 0° C. to 100° C. The compound (XVII) is finally halogenated or sulfonylated to give a compound (II''). The halogenating agent to be used for the halogenation is exemplified by thionyl chloride, phosphorus oxychloride, phosphorus tribromide, etc., and the sulfonylating agent is exemplified by methanesulfoyl chloride, benzenesulfonyl chloride, toluenesulfonyl chloride, etc. The halogenation of (XVII) is usually conducted at about 15° C. to about 100° C., in a suitable solvent such as dichloromethane, chloroform, benzene, toluene, etc. The sulfonylation of (XVII) can be conducted under conditions similar to those used in the halogenation, but it may be more advantageous to carry out the reaction in the presence of a base such as pyridine, triethylamine, etc.

This Method H is particularly useful to prepare optically active starting compounds (II). When an optical isomer of (VIV) is used, a compound (XV) with the same absolute configuration as that of (XIV) is obtained. Cyclization of (XV), however, proceeds with inversion of configuration to yield (XVI) having opposite absolute configuration to (XIV) or (XV). The configuration is retained in the following two steps (XVI)→(XVII)→(II'').

The following are pharmacological test results showing the efficacy of the compound (I) of this invention.

1. Vasodilating Action:

A spiral strip of aorta of a rabbit (2 to 3 mm width, about 3 cm length) was allowed to equilibrate by hanging under 2 g force in a Krebs-Henseleit solution. The solution was saturated with a mixture gas of 97% $O_2$-3% $CO_2$ which was warmed to 37° C. Inhibitory actions of compounds ($10^{-5}$ M) of this invention against contraction of the aorta strip caused by KCl (6.0 mM), norepinephrine (NE) ($10^{-6}$ M) or serotonin (5-HT) ($10^{-6}$ M), by treating the strip with a compound of this invention 30 minutes before the test (15 minutes in the case of 5-HT), are shown in Table 1 as inhibitory percentage.

TABLE 1

| Compound (Working Example No.) | Inhibitory percent against contraction (%) | | |
|---|---|---|---|
| | KCl | NE | 5-HT |
| 1 (2HCl salt) | 82*1 | 95*2 | 52 |
| 2 | 73*1 | 100 | — |
| 3 | 10 | 99 | 91 |
| 5 | 9 | 86 | 100 |
| 6 | 37 | 100 | 81 |
| 7 | 29 | 98 | 81 |
| 8 | 33 | 98 | — |
| 12 | 21 | 100 | — |
| 13 | 24 | 100 | — |
| 15 | 8 | 100 | — |
| 21 | 26 | 99 | — |
| 22 | 14 | 95 | 38 |
| 25 | 9 | 100 | — |
| 27 | 36 | 98 | — |
| 28 | 28 | 100 | — |
| 30 | 33 | 73 | — |

TABLE 1-continued

| Compound (Working Example No.) | Inhibitory percent against contraction (%) | | |
|---|---|---|---|
| | KCl | NE | 5-HT |
| 31 | 30 | 99 | — |

Note:
*[1] means the value in case of treating 3 hours before the test
*[2] means the value in case of treating 2 hours before the test 2. Intracellular $Ca^{++}$ Antagonism:

A spiral strip of aorta of a rabbit (2 to 3 mm width, aobut 3 cm length) was allowed to equilibrate by hanging under 2 g force in a Krebs-Henseleit solution. The solution was saturated with a mixture gas of 97% $O_2$-3% $CO_2$, which was warmed to 37° C. The strip was moved into another Krebs-Henseleit solution containing $Ca^{++}$ OmM and EGTA 5 mM. Five minutes later, caffeine (20 mM) was added to the solution. The resulting contraction of the strip was made as the index of the contraction depending on intracellular $Ca^{++}$. The inhibitory percentage against this contraction by addition of the compounds of this invention is shown in Table 2.

TABLE 2

| Compound (Working Example No.) | concentration (M) | Inhibitory percent (%) |
|---|---|---|
| 1 | $10^{-5}$ | 87 |
|  | $10^{-6}$ | 60 |
| 3 | $10^{-5}$ | 60 |
| 5 | $10^{-5}$ | 58 |
| 10 | $10^{-5}$ | 59 |
| 14 | $10^{-6}$ | 61 |
| 15 | $10^{-6}$ | 58 |
| 18 | $10^{-6}$ | 59 |
| 21 | $10^{-6}$ | 54 |
| 23 | $10^{-6}$ | 42 |
| Control TMB-8 | $10^{-5}$ | 48 |

3. Antihypertensive Action:

Spontaneously hypertensive rats (male, 12 to 13 weeks old, blood pressure before administration of drug was about 200 mmHg) were used in groups of 3 individuals. After measuring tail arterial pressure of these animals by the tail-cuff method, the animals were orally given 3 to 60 mg/kg of each test compound of this invention as 2 ml of its suspension in gum arabic. Blood pressure measurements were made again one hour after administration of each test compound. Difference of blood pressure before and after medication (antihypertensive effects, ΔmmHg) are shown in Table 3.

TABLE 3

| Compound (Working Example No.) | Dose (mg/kg) | Antihypertensive effect (Δ mm Hg) |
|---|---|---|
| 1 (2HCl salt) | 10 | 50 |
|  | 3 | 30 |
| 2 | 60 | 44 |
| 3 | 60 | 45 |
| 6 | 60 | 43 |
| 8 | 60 | 35 |
| 10 | 10 | 23 |
| 12 | 3 | 20 |
| 13 | 3 | 27 |
| 14 | 3 | 54 |
| 15 | 3 | 49 |
| 17 | 3 | 26 |
| 18 | 3 | 32 |
| 22 | 3 | 23 |
| 24 | 60 | 60 |

TABLE 3-continued

| Compound (Working Example No.) | Dose (mg/kg) | Antihypertensive effect (Δ mm Hg) |
|---|---|---|
| 25 | 60 | 81 |
| 28 | 3 | 20 |
| 30 | 3 | 21 |
| 31 | 3 | 21 |

4. Protective action on ischemic cardiovascular tissue damages:

4-1. Effect on the ischemia-reperfusion-induced ventricular arrhythmia in rats:

Male Sprague-Dawley rats, 9 to 10 week old, were orally given the compounds or tap water at a volume of 5 ml/kg. After one hour, the animals were anesthetized with sodium pentobarbital (50 mg/kg, by intraperitoneal injection), and they were subjected to thoracotomy under artificial respiration, and the left anterior descending coronary artery was occluded for five minutes. The incidences of ventricular tachycardia, ventricular fibrillation and cardiac arrest for ten minutes after reperfusion of the blood were calculated. As shown in Table 4, the compound of Example 1 at 3, 10, and 20 mg/kg given orally inhibited the incidences of cardiac functional abnormalities in a dose-dependent manner.

TABLE 4

| Test Group | Dose mg/kg, p.o. | Ventricular tachycardia | Ventricular fibrillation | Cardiac arrest |
|---|---|---|---|---|
| Control | — | 18/18[note] | 17/18 | 8/18 |
| Compound of Example 1 (2HCl salt) | 3 | 7/9 | 5/9* | 2/9 |
|  | 10 | 7/11** | 5/11** | 4/11 |
|  | 20 | 2/5** | 0/5** | 0/5 |

[note] The number of denominator shows the number of rats used and that of numerator shows the number of rats which induced the changes in cardiac function.
Significance test: $X^2$-test: *$P < 0.05$ **$P < 0.01$ 4-2. Effect on acute renal failure in rats:

Male sprague-Dawley rats, 6 week old, were orally given the compunds or tap water at a volume of 5 ml/kg. After one hour, the animals were anesthetized with sodium pentobarbital. The animals were subjected to laparotomy, and the left renal artery was clamped completely for one hour. The clamp was undone, and the incision was closed. The animals were again given orally the compounds or tap water 20 hours later. Further four hours later, the animals were again anesthetized, and the blood was obtained from the abdominal aorta. The plasma was separated for measurement of urea nitrogen (BUN).

As shown in Table 5, the compound of Example 1 given orally at a volume of 1, 3 and 10 mg/kg inhibited the increase in BUN.

TABLE 5

| Test group | Dose mg/kg, p.o. | Number of rats | BUN mg/dl |
|---|---|---|---|
| Control | — | 14 | 27 ± 1 |
| Compound of Example 1 (2HCl salt) | 1 | 5 | 24 ± 0.5* |
|  | 3 | 5 | 22 ± 2* |
|  | 10 | 5 | 23 ± 0.5* |

Significance test (Student's t-test): *$P < 0.05$

5. Acute toxicity:

Male Wister rats aged five weeks (five animals/group) were orally given the test compounds (Example No. 1, 14, 15 and 18) suspended in a 5% solution of gum arabic. Each animal so treated was observed over a period of seven days. The acute toxicity (LD$_{50}$) of each compound was not less than 300 mg/kg.

The following Examples, Formulation Examples and Reference Examples further illustrate this invention in more detail, and all the melting points mentioned therein are those measured by the hot plate method and are uncorrected.

EXAMPLE 1

Method A: A mixture of 2-(3-bromopropyl)-6,7,8,9-tetrahydro-2H-naphtho[2,3-b][1,4]oxazin-3(4H)-one (3.1 g), 1-(4-fluorophenyl)piperazine (2.3 g), triethylamine (1.5 ml) and N,N-dimethylformamide (DMF)(100 ml) was stirred at 80° C. for 1.5 hour, which was diluted with ice-water and subjected to extraction with ethyl acetate. The ethyl acetate layer was washed with water and dried (MgSO$_4$), from which the solvent was distilled off. The residue was recrystallized from chloroform-ethyl acetate to give 2.4 g (59.3%) of 2-{3-[4-(4-fluorophenyl)-1-piperazinyl]propyl}-6,7,8,9-tetrahydro-2H-naphtho[2,3-b][1,4]oxazin-3(4H)-one as colorless crystals, m.p. 164°-165° C.

Analysis—Calc'd. for C$_{25}$H$_{30}$FN$_3$O$_2$: C,70.90; H,7.14; N, 9.92. Found: C,70.72; H,7.02; N,9.88.

The crystals were dissolved in chloroform-methanol (1:2, v/v), to which was added methanolic hydrogen chloride, followed by concentration. The resultant crystals were further recrystallized from methanol to give dihydrochloride as colorless crystals, m.p.150°-151° C.

Analysis—Calc'd. for C$_{25}$H$_{30}$FN$_3$O$_2$·2HCl:C,60.48;H,6.50;N,8.46. Found: C,60.35;H,6.65;N,8.42.

Method B: In a mixture of acetic acid (15 ml) and water (2.5 ml) was dissolved methyl 5-[4-(4-fluorophenyl)-1-piperazinyl]-2-(5,6,7,8-tetrahydro-3-nitro-2-naphthyloxy)valerate (4.1 g). To the solution was added little by little iron powder (1.9 g) whil stirring. The reaction was allowed to proceed for 30 minutes, followed by stirring at 80° C. for further 15 minutes. The resultant precipitate was filtered off, and the filtrate was concentrated. To the concentrate was added water, which was neutralized with an aqueous solution of sodium carbonate, followed by extraction with chloroform (then precipitated inorganic substances were filtered off). The chloroform layer was washed with water and dried (MgSO$_4$). The concentrate was recrystallized from chloroform—ethyl acetate to give 1.54 g (43.1%) of 2-{3-[4-(4-fluorophenyl)-1-piperazinyl]propyl}-6,7,8,9-tetrahydro-2H-naphtho[2,3-b][1,4]oxazin-3(4H)-one as crystals, m.p. 164°-165° C. This product was in good agreement with the authentic sample obtained by Method A.

EXAMPLE 2 to 22

Compounds shown in Table 6 were obtained by similar procedure to Example 1.

TABLE 6

| Example NO. | R$^1$, R$^2$ | R$^4$, R$^5$ | n | Method | Yield (%) | Recrystallization solvent | mp (°C.) |
|---|---|---|---|---|---|---|---|
| 2 | H, H | 4-F, H | 3 | A | 36.1 | AcOEt—Et$_2$O | 142-143 |
| 3 | 6-CH$_3$, H | 4-F, H | 3 | A | 94.7 | EtOH—AcOEt | 174-175 |
| 4 | 6-CH$_3$, H | 3-CF$_3$, H | 3 | A | 70.0 | AcOEt—Et$_2$O | 144-145 |
| 5 | 6-CH$_3$, H | 4-F, H | 2 | A | 80.4 | AcOEt—Et$_2$O | 199-200 |
| 6 | 6-NO$_2$, H | 4-F, H | 3 | A | 80.6 | AcOEt—Et$_2$O | 153-154 |
| 7 | 6-Cl, H | 4-F, H | 3 | A | 72.1 | AcOEt—Et$_2$O | 189-190 |
| 8 | 7-C$_2$H$_5$OCO, H | 4-F, H | 3 | A | 34.8 | AcOEt—Et$_2$O | 147-148 |
| 9 | 5-CH$_3$, 8-i-Pr | 4-F, H | 3 | B | 35.7 | MeOH—AcOEt | 192-193 |
| 10 | 5,6-(CH$_2$)$_4$— | 4-F, H | 3 | B | 19.3 | AcOEt | 176-177 |
| 11 | 6,7-(CH$_2$)$_4$— | 4-F, H | 2 | B | 34.8 | AcOEt | 152-153 |
| 12 | 6,7-(CH$_2$)$_3$— | 4-F, H | 3 | A | 90.9 | CH$_2$Cl$_2$—AcOEt | 186-187 |
| 13 | 6,7-OCH$_2$O— | 4-F, H | 3 | B | 77.4 | AcOEt—Et$_2$O | 194-195 |
| 14 | 6,7-(CH$_2$)$_4$— | 3-F, H | 3 | A | 54.1 | CHCl$_3$—AcOEt | 158-159 |
| 15 | 6,7-(CH$_2$)$_4$— | 2-CH$_3$O, H | 3 | A | 90.0 | CHCl$_3$—AcOEt | 146-147 |
| 16 | 6,7-(CH$_2$)$_4$— | 3-CF$_3$, H | 3 | A | 71.2 | CHCl$_3$—AcOEt | 196-197 |
| 17 | 6,7-(CH$_2$)$_4$— | 4-CH$_3$, H | 3 | A | 31.9 | CHCl$_3$—AcOEt | 180-181 |
| 18 | 6,7-(CH$_2$)$_4$— | H, H | 3 | A | 53.9 | CHCl$_3$—AcOEt | 178-179 |
| 19 | 6-i-Pr, 7-CH$_3$ | 4-F, H | 3 | B | 38.9 | CHCl$_3$—AcOEt | 174-175 |
| 20 | 6,7-(CH$_2$)$_4$— | 3-Cl, 4-CH$_3$ | 3 | A | 45.7 | CHCl$_3$—AcOEt | 174-175 |
| 21 | 6,7-(CH$_2$)$_4$— | 4-OH, H | 3 | A | 64.8 | CHCl$_3$—MeOH | 217-218 |
| 22 | 6,7-(CH$_2$)$_4$— | 4-F, H | 4 | B | 39.7 | CHCl$_3$—AcOEt | 160-161 |

EXAMPLE 23

A solution of 2-{3-[4-(4-fluorophenyl)-1-piperazinyl]propyl}-6,7,8,9-tetrahydro-2H-naphtho[2,3-b][b 1,4]oxazin-3(4H)-one (424 mg) in DMF (6 ml) was added dropwise at 0° C. to a mixture of DMF (4 ml) and 60% sodium hydride in oil (60 mg). The resultant mixture was stirred for 10 minutes, to which was added dropwise methyl iodide (0.1 ml), followed by stirring at 0° C. for 30 minutes. The resultant was diluted with water and subjected to extraction with ether. The ether layer was washed with an aqueous saline, followed by drying (MgSO$_4$). The solvent was distilled off, and the residue was purified by means of silica gel chromatography, followed by crystallization from ether to give 276 mg (63.0%) of 2-{3-[4-(4-fluorophenyl)-1-piperazinyl]propyl}-6,7,8,9-tetrahydro-4-methyl-2H-naphtho[2,3-b][1,4]oxazin-3(4H)-one as colorless crystals, m.p. 98°-98.5° C.

Analysis—Calc'd. for $C_{26}H_{32}FN_3O_2$: C, 71.37; H,7.37; N,9.60. Found: C,71.30; H,7.33; N,9.65.

EXAMPLE 24

In a mixture of methanol (80 ml) and tetrahydrofuran (20 ml) was dissolved 2-{3-[4-(4-fluorophenyl)-1-piperazinyl]propyl}-6-nitro-2H-1,4-benzoxazin-3(4H)-one (2.03 g). To the solution was added 10% Pd - C (50% wet, 0.6 g) to conduct catalytic reduction. After the absorption of hydrogen finished, the catalyst was filtered off, and the filtrate was concentrated. The residue was crystallized from ethanol to give 1,85 g (98.2%) of 6-amino-2-{3-[4-(4-fluorophenyl)-1-piperazinyl]propyl}-2H-1,4-benzoxazin-3(4H)-one, m.p. 158°–159° C.

Analysis—Calc'd. for $C_{21}H_{25}FN_4O_2$: C,65.61; H,6.55; N,14.57. Found: C,65.26; H,6.46; N,14.33.

EXAMPLE 25

To a solution of 6-amino-2-{3-[4-(4-fluorophenyl)-1-piperazinyl]propyl}-2H-1,4-benzoxazin-3(4H)-one (500 mg) in pyridine (5 ml) was added acetic anhydride (0.18 ml) while stirring. The mixture was stirred at room temperature for further 4 hours, which was then poured into ice-water. Precipitated crystals were collected by filtration, followed by recrystallization from dichloromethane-ethyl acetate to give 397 mg (71.5%) of 6-acetamido-2-{3-[4-(4-fluorophenyl)-1-piperazinyl]propyl}-2H-1,4-benzoxazin-3(4H)-one, m.p. 111°–112° C.

Analysis—Calc'd. for $C_{23}H_{27}FN_4O_3 \cdot \frac{1}{2}H_2O$: C,63.43; H,6.48; N,12.86. Found: C,63.57; H,6.44; N,12.74.

EXAMPLE 26

In a manner similar to that of Method A of Example 1, was obtained 6,7,8,9-tetrahydro-2-{3-[4-(3,4-methylenedioxphenyl)-1-piperazinyl]propyl}-2H-naphtho[2,3-b][1,4]oxazin-3(4H)-one, m.p. 152°–153° C. (recrystallization from chloroform-ethyl acetate). The yield was 50.5%.

EXAMPLE 27

In a manner similar to that of Method A of Example 1, was obtained 2-{3-[4-(4-fluorophenyl)-1-piperazinyl]propyl}-6-trifluoromethyl-2H-1,4-benzoxazin-3(4H)-one, m.p. 156°–157° C. (recrystallization from chloroform-ethyl acetate). The yield was 63.5%.

EXAMPLE 28

In a manner similar to that of Method A of Example 1, was obtained 5,6-cyclopenteno-2-{3-[4-(4-fluorophenyl)-1-piperazinyl]propyl}-2H-1,4-benzoxazin-3(4H)-one, m.p. 171°–172° C. (recrystallized from chloroform-ethyl acetate). The yield was 76.7%.

EXAMPLE 29

In a mixture of methanol (10 ml) and tetrahydrofuran (10 ml) was dissolved methyl 5-[4-(4-fluorophenyl)-1-piperazinyl]-2-(5,6,7,8-tetrahydro-3-nitro-2-naphthyloxy) valerate. The solution was subjected to catalytic reduction in the presence of 5% palladium carbon (50% wet, 0.3 g). The catalyst was filtered off, and the filtrate was concentrated. The concentrate was recrystallized from chloroform-ethyl acetate to give 0.53 g (60.7%) of 2-{3-[4-(4-fluorophenyl)-1-piperazinyl]propyl}-6,7,8,9-tetrahydro-2H-naphtho[2,3-b][1,4]oxazin-3(4H)-one as colorless crystals, m.p. 164°–165° C. This product was in agreement with the authentic sample obtained in Example 1.

EXAMPLE 30

A mixture of (S)-6,7,8,9-tetrahydro-2-(3-mesyloxypropyl)-2H-naphtho[2,3-b][1,4]oxazin-3(4H)-one (1.02g), 1-(4-fluorophenylpiperazine) (0.83g), triethylamine (0.43 ml) and dimethylformamide (15 ml) was stirred at 70° C. for 2 hours. The solvent was distilled off and the residue was purified by column chromatography on silica gel (60 g) with ethyl acetate-hexane (3:1, v/v) to yield crystals of (S)-(-)-2-{3-[4-(4-fluorophenyl)-1-piperazinyl]propyl}-6,7,8,9-tetrahydro-2H-naphtho[2,3-b][1,4]oxazin-3(4H)-one (0.76 g, 59.6%). Repeated recrystallization from MeOH gave colorless crystals, m.p. 155.5°–156.6° C. $[\alpha]_D^{26} -19.9°$ (c=1.2, $CHCl_3$).

Analysis—Calc'd for $C_{25}H_{30}FN_3O_2$: C, 70.90;H, 7.14; N, 9.92. Found: C, 70.63;H, 7.19; N, 9.91.

EXAMPLE 31

Treatment of (R)-6,7,8,9-tetrahydro-2-(3-mesyloxypropyl)-2H-naphtho[2,3-b][1,4]oxazin-3(4H)-one with 1-(4-fluorophenylpiperazine) in the same manner as in Example 30 gave (R)-(+)-2-{3-[4-(4-fluorophenyl)-1-piperazinyl]propyl}-6,7,8,9-tetrahydro-2H-naphtho[2,3-b][1,4]oxazin-3(4H)-one in 66.5% yield, m.p. 155°–156° C. $[\alpha]_D^{26} +19.9°$ (c=0.7, $CHCl_3$).

Analysis—Calc'd for $C_{25}H_{30}FN_3O_2$: C, 70.90;H, 7.14;N, 9.92. Found: C, 70.60;H, 7.14;N, 9.89.

EXAMPLE 31

Treatment of (R)-6,7,8,9-tetrahydro-2-(3-mesyloxypropyl) -2H-namptho [2,3-b] [1,4]oxazin-3(4H)-one with 1-(4-fluorophenylpiperazine) in the same manner as in Example 30 gave (R)-(+)-2-{3-[4-(4-fluorophenyl)-1-piperazinyl]propyl}- 6,7,8,9-tetrahydro-2H-naphtho [2,3-b] [1,4]oxazin-3(4H)-one in 66.5% yield, m.p. 155°–156° C. $[\alpha]_D^{26}+19.9°$ (c=0.7, $CHCl_3$).

Analysis—Calc'd for $C_{25}H_{30}FN_3O_2$: C, 70.90; H, 7.14; N, 9.92. Found: C, 70.60; H, 7.14; N, 9.89.

EXAMPLE 32

2-{3-[4-(4-fluorophenyl)-1-piperazinyl]propyl}-6-methoxy-2H-1,4-benzoxazin-3(4H)-one was obtained in a manner similar to Method A of Example 1.

The yield was 87.2%. m.p. 153°–154° C. (recrystallization from methanol).

FORMULATION EXAMPLE

When the compound (I) of this invention is used as an antihypertensive drug, the following exemplary formulation is employed.

A. Tablets:

| (1) 2-{3-[4-(4-fluorophenyl)-1-piperazinyl]propyl}-6,7,8,9-tetrahydro-2H—naphtho[2,3-b][1,4]oxazin-3(4H)—one | 3 g |
|---|---|
| (2) Lactose | 97 g |
| (3) Corn starch | 29 g |
| (4) Magnesium stearate | 1 g |
| 1000 Tablets | 130 g |

The whole amounts of (1) and (2) are mixed with 17 g of (3) and the mixture is granulated with a paste prepared from 7 g of (3). Then 5 g of (3) and the whole amount of (4) are added to the granule. The whole mixture is compression-molded on a compression tableting machine to give 1000 tablets each containing 3 mg of (1).

B. Capsules:

| (1) 2-{3-[4-(4-fluorophenyl)-1-piperazinyl]propyl}-6,7,8,9-tetrahydro-2H—naphtho[2,3-b][1,4]oxazin-3(4H)—one | 3 g |
|---|---|
| (2) Lactose | 142 g |
| (3) Microcrystalline cellulose | 70 g |
| (4) Magnesium stearate | 5 g |
| 1000 capsules | 220 g |

The whole amounts of the above components are mixed and filled into 1000 gelatin capsules to give capsules each containing 3 mg of (1).

REFERENCE EXAMPLE 1

A mixture of 2-amino-4-chlorophenol (0.74 g), methyl 2,5-diboromovalerate (1.40 g), powdery potassium carbonate (0.68 g) and acetone (20 ml) was stirred for 6 hours under reflux, to which was added water (30 ml), followed by extraction with ethyl acetate. The ethyl acetate layer was washed with water and dried (MgSO$_4$), then the solvent was distilled off. The residue was purified by means of silica gel chromatography [eluted with hexane-ethyl acetate (3:1)], followed by crystallization from ether to obtain 0.47 g (30.2%) of 2-(3-bromopropyl)-6-chloro-2H-1,4-benzoxazin-3(4H)-one as crystals, m.p. 157°–158° C.

Analysis—Calc'd. for $C_{11}H_{11}BrClNO_2$: C,43.38; H,3.64; N,4.60. Found: C,43.63; H,3.55; N,4.90.

Reference Example 2 to 4

By a process similar to that in Reference Example 1, the compounds shown in Table 7 were obtained.

TABLE 7

| Reference Ex. No. | R$^1$ | n | m.p. (°C.) |
|---|---|---|---|
| 2 | 6-CH$_3$ | 3 | 128–129 |
| 3 | 6-NO$_2$ | 3 | 150–151 |
| 4 | 6-CH$_3$ | 2 | 183–184 |

REFERENCE EXAMPLE 5

A mixture of 2-nitrophenol (0.7 g), powdery potassium carbonate (0.7 g), methyl 2,5-dibromovalerate (1.37 g) and dimethylformamide (10 ml) was stirred at room temperature for 4 hours, to which was added ice-water, followed by extraction with ether. The ether layer was washed with water and dried (MgSO$_4$), then the solvent was distilled off. The residue was purified by means of silica gel chromatography [eluted with hexane-ethyl acetate (1:4)] to obtain methyl 5-bromo-2-(2-nitrophenoxy)valerate as an oily product. The yield was 1.30 g (77.8%).

IR (Neat): 1740 cm$^{-1}$, NMR(CDCl$_3$)δ: 1.97–2.39(4H,m), 3.50 (2H,m), 3.77(3H,s), 4.83(1H,t,J=5.1 Hz), 6.87–7.95(4H,m).

The oily product (0.67 g) obtained as above was dissolved in methanol (15 ml), which was subjected to catalytic reduction in the presence of 10% Pd-C(50% wet, 0.24 g). The catalyst was filtered off, and the filtrate was concentrated. The concentrate was purified by means of silica gel chromatography [eluent: hexane-ethyl acetate (1:3)], followed by crystallization from ether to give 0.31 g (57%) of 2-(3-bromopropyl)-2H-benzoxazin-4(3H)-one as crystals, m.p. 90°–92° C.

Analysis—Calc'd. for $C_{11}H_{12}BrNO_2$: C,48.91; H,4.48; N,5.19. Found: C,48.97; H,4.35; N,5.13.

REFERENCE EXAMPLE 6

By a process similar to that of Reference Example 5, ethyl 3-hydroxy-4-nitrobenzoate was allowed to react with methyl 2,5-dibromovalerate to give methyl 5-bromo-2-(5-ethoxycarbonyl-2-nitrophenoxy)valerate as an oily product (yield: 80.2%). This product was subjected to catalytic reduction to obtain ethyl 2-(3-bromopropyl)-3,4-dihydro-3-oxo-2H-1,4-benzoxazine-7-carboxylate, m.p. 118°–119° C. The yield was 90.7%.

Analysis —Calc'd. for $C_{14}H_{16}BrNO_4$: C,49.14; H,4.71; N,4.09. Found: C,49.53; H,4.75; N,4.09.

REFERENCE EXAMPLE 7

In a manner similar to that of Reference Example 5, 5,6,7,8-tetrahydro-3-nitro-2-naphthol was allowed to react with methyl 2,5-dibromovalerate to obtain methyl 5-bromo-2-(5,6,7,8-tetrahydro-3-nitro-2-naphthyloxy)valerate as crystals, m.p. 73°–74° C. (recrystallized from isopropylether)). The yield was 71.5%.

Analysis—Calc'd. for $C_{16}H_{20}BrNO_5$: C,49.76; H,5.22; N,3.63. Found: C,49.63; H,5.26; N,3.55.

The crystals obtained as above were subjected to catalytic reduction to obtain 2-(3-bromopropyl)-6,7,8,9-tetrahydro-2H-naphtho[2,3-b][1,4]oxazin-3(4H)-one as crystals, m.p. 139°–140° C. (recrystallized from ethyl acetate). The yield was 81.1%.

Analysis—Calc'd. for $C_{15}H_{18}BrNO_2$: C,55.57; H,5.60; N,4.32. Found: C,55.58; H,5.41; N,4.29.

REFERENCE EXAMPLE 8

A mixture of methyl 5-bromo-2-(5,6,7,8-tetrahydro-3-nitro-2-naphthyloxy)valerate (5.0 g), 1-(4-fluorophenyl)piperazine (2.45 g), dimethylformamide (40 ml) and triethylamine (1.99 g) was stirred at 80° C. for 2 hours, which was cooled and then diluted with water, followed by extraction with chloroform. The chloroform layer was washed with water and dried (MgSO$_4$). The solvent was then distilled off, and the residue was purified by means of silica gel chromatography [eluent: hexane-ethyl acetate (1:1)] to obtain 4.51 g (71.8%) of methyl 5-[4-(4-fluorophenyl)-1-piperazinyl]-2-(5,6,7,8-tetrahydro-3-nitro-2-naphthyloxy) valerate as an oily product. IR(Neat): 1755, 1620 cm$^{-1}$. NMR(CDCl$_3$)δ: 1.57–2.22(8H,m), 2.35–2.82(10H,m), 2.96–3.15 (4H,m), 3.73(3H,s), 4.80(1H,t,J=5.7 Hz), 6.55(1H,s), 6.69–7.05(4H,m), 7.58(1H,s).

REFERENCE EXAMPLE 9

In a manner similar to that of Reference Example 5, 2-isopropyl-5-methyl-6-nitrophenol was allowed to react with methyl 2,5-dibromovalerate to give methyl 5-bromo-2-(2-isopropyl-5-methyl-2-nitrophenoxy)valerate, which was then allowed to react, in a manner similar to that of Reference Example 8, with 1-(4-fluorophenyl)piperazine to obtain methyl 5-[4-(4-fluorophenyl)-1-piperazinyl]-2-(2-isopropyl-5-methyl-6-nitrophenoxy)valerate as an oily product. The overall yield was 33.9%. IR(Neat): 1745 cm$^{-1}$. NMR(CDCl$_3$)δ: 1.20(3H,d,J=7 Hz), 1.18(3H,d,J=7 Hz), 1.44–2.13 (4H,m), 2.25(3H,s), 2.40(2H,t,J=6.6 Hz), 2.47–2.69(4H,m), 2.99–3.19(4H,m), 3.37(1H,m), 3.70(3H,s), 4.49(1H,t,J=6.6 Hz), 6.73–7.32(6H,m).

REFERENCE EXAMPLE 10 In a manner similar to that of Reference Example 5, 4-isopropyl-5-methyl-2-nitrophenol was allowed to react with methyl 2,5-dibromovalerate to give methyl 2,5-dibromo-2-(4-isopropyl-5-methyl-2-nitrophenoxy)-valerate, which was then allowed to react, in a manner similar to that of Reference Example 8, with
1-(4-fluorophenyl)piperazine to obtain methyl
5-[4-(4-fluorophenyl)-1-piperazinyl]-2-(4-isopropyl-5-methyl-2-nitrophenoxy)valerate as an oily product. The overall yield was 50.2%.

NMR(CDCl$_3$)δ: 1.17(3H,d,J=6.5 Hz), 1.21(3H,d,J=6.5 Hz), 1.57–2.24(4H,m), 2.30(3H,s), 2.47(2H,t,J=6.0 Hz), 2.50–2.72 (4H,m), 2.95–3.19(5H,m), 3.73(3H,s), 4.82(1H,t,J=6 Hz), 6.62 (1H,s), 6.71–7.08(4H,m), 7.73(1H,s)

REFERENCE EXAMPLE 11

In a manner similar to that of Reference Example 5, 4,5-methylenedioxy-2-nitrophenol was allowed to react with methyl 2,5-dibromovalerate to give methyl 5-bromo-2-(4,5-methylenedioxy-2-nitrophenoxy)valerate, which was then allowed to react, in a manner similar to that of Reference Example 8, with 1-(4-fluorophenyl)-piperazine to obtain methyl 5-[4-(4-fluorophenyl)-1-piperazinyl]-2-(4,5-methylenedioxy-2-nitrophenoxy)-valerate as crystals, m.p. 98°–99° C. The overall yield was 15.6%.

Analysis—Calc'd. for C$_{23}$H$_{26}$FN$_3$O$_7$: C,58.10; H,5.51; N,8.84. Found: C,58.05; H,5.41; N,8.81.

REFERENCE EXAMPLE 12

In a manner similar to that of Reference Example 5, 5,6,7,8-tetrahydro-1-nitro-2-naphthol was allowed to react with methyl 2,5-dibromovalerate to give methyl 5-bromo-2-(5,6,7,8-tetrahydro-1-nitro-2-naphthyloxy)-valerate, which was then allowed to react, in a manner similar to that of Reference Example 8, with 1-(4-fluorophenyl)piperazine to obtain methyl 5-[4-(4-fluorophenyl)-1-piperazinyl]-2-(5,6,7,8-tetrahydro-1-nitro-2-naphthyloxy)valerate as an oily product. The overall yield was 65.1%. NMR(CDCl$_3$)δ: 1.55–2.17(8H,m), 2,41(2H,5,J=7.2 Hz), 2.52–2.81(8H,m), 2.96–3.14(4H,m), 3.72(3H,s), 4.67(1H,t,J=6 Hz), 6.55–7.11 (6H,m)

REFERENCE EXAMPLE 13

In a manner similar to that of Reference Example 5, 5,6,7,8-tetrahydro-3-nitro-2-naphthol was allowed to react with methyl 2,4-dibromobutyrate to obtain methyl 4-bromo-2-(5,6,7,8-tetrahydro-3-nitro-naphthyloxy)butyrate as pale yellow crystals, m.p. 99°–100° C. The yield was 66.2%.

Analysis—Calc'd. for C$_{15}$H$_{18}$BrNO$_5$: C,48.40; H,4.87; N,3.76. Found: C,48.44; H,4.90; N,3.77.

The crystals obtained as above was allowed to react, in a manner similar to that of Reference Example 8, with 1-(4-fluorophenyl)piperazine to obtain methyl 4-[4-(4-fluorophenyl)-1-piperazinyl]-2-(5,6,7,8-tetrahydro-3-nitro-2-naphthyloxy)butyrate as an oily product. The yield was 97.2%. NMR(CDCl$_3$)δ: 1.68–1.93(4H,m), 2.21(2H,t,J=6 Hz), 2.51–2.86(10H,m), 2.97–3.15(4H,m), 3.71(3H,s), 4.85(1H,t, J=6 Hz), 6.61(1H,s), 6.70–7.05(4H,m), 7.56(1H,s).

REFERENCE EXAMPLE 14

In a manner similar to that of Reference Example 5, 6-nitro-5-indanole was allowed to react with methyl 2,5-dibromovalerate to give methyl 5-bromo-2-(6-nitro-5-indanyloxy)valerate, which was then subjected to catalytic reduction to obtain 2-(3-bromopropyl)-6,7-cyclopenteno-2H-1,4-benzoxazin-3(4H)-one as crystals, m.p. 154°–155° C.

Analysis—Calc'd. for C$_{14}$H$_{16}$BrNO$_2$: C,54.21; H,5.20; N,4.52. Found: C,54.38; H,5.18; N,4.66.

REFERENCE EXAMPLE 15

In a manner similar to that of Reference Example 5, 5,6,7,8-tetrahydro-3-nitro-2-naphthol was allowed to react with methyl 2,6-dibromohexanoate to give methyl 6-bromo-2-(5,6,7,8-tetrahydro-3-nitro-2-naphthyloxy)-hexanoate as an oily product, which was then allowed to react, in a manner similar to that of Reference Example 8, with 1-(4-fluorophenyl)piperadine to obtain methyl 6-[4-(4-fluorophenyl)-1-piperazinyl]-2-(5,6,7,8-tetrahydro-3-nitro-2-naphthyloxy) hexanoate as an oily product. The overall yield was 79.4%.

IR(Neat): 1750 cm$^{-1}$. NMR(CDCl$_3$)δ: 1.63–2.20(10H,m), 2.31–2.86(10H,m), 3.0–3.20(4H,m), 3.73(3H,s), 4.69(1H,t,J=6 Hz), 5.57(1H,s), 6.77–7.07(4H,m), 7.57(1H,s)

REFERENCE EXAMPLE 16

To a mixture of 3-amino-5,6,7,8-tetrahydro-2-naphthol hydrobromide (1.70 g), sodium hydrogencarbonate (1.46 g), ethyl acetate (15 ml) and water (10 ml) was added under ice-cooling while stirring a solution of 2,5-dibromovaleryl chloride (1.94 g) in ethyl acetate (6 ml). The whole mixture was stirred for further 30 minutes. The ethyl acetate layer was separated, and the aqueous layer was extracted with ethyl acetate. The combined ethyl acetate layer was washed with an aqueous saline. solution, then dried (MgSO$_4$), followed by distilling off the solvent to obtain 3-(2,5-dibromovaleryl)amino-5,6,7,8-tetrahydro-2-naphthol.

This compound was dissolved in dimethylformamide (20 ml). To the solution was added powdery potassium carbonate (1.2 g), and the mixture was stirred at room temperature for 1.5 hour. To the resultant was added water, and precipitated crystals were collected by filtration, washed with water and dried, followed by recrystallization from ethyl acetate to obtain 1.53 g (67.8%) of 2-(3-bromopropyl)-6,7,8,9-tetrahydro-2H-naphtho [2,3-b][1,4]oxazin-3(4H)-one as crystals, m.p. 139°–140° C. This compound was found to be identical with the product obtained in Reference Example 7.

REFERENCE EXAMPLE 17

In a manner similar to that of Reference Example 16, 2-amino-4-trifluoromethylphenol.hydrochloride was allowed to react with 2,5-dibromovaleryl chloride, followed by subjecting the resultant to ring-closure reaction to obtain 2-(3-bromopropyl)-6-trifluoromethyl-2H-1,4-benzoxazin-3(4H)-one as crystals, m.p. 123°–124° C. (recrystallized from isopropylether). The yield was 35.6%.

Analysis—Calc'd. for $C_{12}H_{11}BrF_3NO_2$: C,42.63; H,3.28; N,4.14. Found: C,42.56; H,3.36; N,4.08.

REFERENCE EXAMPLE 18

In a manner similar to that of Reference Example 16, 4-amino-5-indanole.hydrobromide was allowed to react with 2,5-dibromovaleryl chloride, followed by subjecting the resultant to ring-closure reaction to obtain 2-(3-bromopropyl)-5,6-cyclopenteno-2H-1,4-benzoxazin-3(4H)-one as crystals, m.p. 154.5°–155.5° C. The yield was 60.0%.

Analysis—Calc'd. for $C_{14}H_{16}BrNO_2$: C,54.21; H,5.20; N,4.52. Found: C,54.05; H,5.16; N,4.51.

REFERENCE EXAMPLE 19

A mixture of (R)-2-chloro-4-methoxycarbonylbutyric acid (3.85 g) and thionyl chloride (2.4 ml) was stirred at 75° C. for 1 hour and the excess thionyl chloride was removed by distillation to give (R)-2-chloro-4-methoxycarbonylbutyryl chloride as an oil. A solution of this oil in ethyl acetate (10 ml) was then added dropwise to a stirred and ice-cooled mixture of 3-amino-5,6,7,8-tetrahydro-2-naphthol hydrobromide (5.20 g), sodium bicarbonate (4.48 g), water (20 ml) and ethyl acetate (30 ml). The whole was stirred at 0° C. for 1.5 hour and the organic layer was separated. The aqueous layer was further extracted with ethyl acetate. The combined organic layer was washed with water and dried over magnesium sulfate. Evaporation of the solvent gave methyl (R)-4-chloro-4-[N-(3-hydroxy-5,6,7,8-tetrahydro-2naphthyl)carbamoyl]butyrate as an oil (6.20 g). A mixture of this oil, powdered potassium carbonate (2.95 g) and dimethylformamide (20 ml) was then stirred at room temperature for 1.5 hour. Dilution with water gave methyl (S)-3-(3,4,6,7,8,9-hexahydro-3-oxo-2H-naphtho[2,3-b][1,4]oxazin-2-yl)propionate was crystals (2.52 g, 40.9%). Purification by column chromatography on silica gel with ethyl acetate-hexane (3:2, v/v), followed by recrystallization from ethyl acetate-ethyl ether gave colorless crystals (2.22 g, 36.0%), m.p. 138°–139° C. $[\alpha]_D^{26} - 7.8°$ (c=0.3, CHCl$_3$).

Analysis—Calc'd. for $C_{16}H_{19}NO_4$: C, 66.42; H, 6.62;N, 4.84. Found: C, 66.21;H, 6.45;N, 4.94.

REFERENCE EXAMPLE 20

Starting from (S)-2-chloro-4-methoxycarbonylbutyric acid instead of (R)-isomer used in Example 19, methyl (R)-3-(3,4,6,7,8,9-hexahydro-3-oxo-2H-naphtho[2,3-b][1,4]oxazin-2-yl)propionate in 21.7% yield, m.p. 137°–138° C. $[\alpha]_D^{26} + 10.3°$ (c=0.5, CHCl$_3$).

Analysis—Calc'd. for $C_{16}H_{19}NO_4$: C, 66.42;H, 6.62; N, 4.84. Found: C, 66.25;H, 6.67; N, 4.95.

REFERENCE EXAMPLE 21

To a stirred and ice-cooled suspension of lithium aluminum hydride (0.51 g) in dry tetrahydrofuran (20 ml), was added dropwise a solution of methyl (S)-3-(3,4,6,7,8,9-hexahydro-3-oxo-2H-naphtho[2,3-b][1,4]oxazin-2-yl)propionate (1.75 g) in dry tetrahydrofuran (10 ml). The whole was stirred at 0° C. for 1.5 hour and quenched with water. After neutralization with 4N-HCl, the insoluble material was filtered off. The filtrate was extracted with ethyl acetate, and the ethyl acetate layer was washed with water and dried over magnesium sulfate. After evaporation of the solvent, the residue was purified by column chromatography on silica gel (60 g) with ethyl acetate-hexane (3:1, v/v) to yield (S)-6,7,8,9-tetrahydro-2-(3-hydroxypropyl)-2H-naphtho[2,3-b][1,4]oxazin-3(4H)-one as colorless needles (1.56 g, 98.7%), m.p. 139°–140° C. $[\alpha]_D^{26} + 1.4°$ (c=0.5, CHCl$_3$).

Analysis—Calc'd. for $C_{15}H_{19}NO_3$: C, 68.94;H, 7.33;N, 5.36. Found: C, 68.76;H, 7.3;N, 5.41.

REFERENCE EXAMPLE 22

Reduction of methyl(R)-3-(3,4,6,7,8,9-hexahydro-3-oxo-2-H-naphtho[2,3-b][1,4]oxazin-2-yl)propionate in the same manner as in Reference Example 21 gave (R)-6,7,8,9-tetrahydro-2-(3-hydroxypropyl)-2H-naphto[2,3-b][1,4]oxazin-3(4H)-one in 94.3% yield. m.p. 141°–142° C. $[\alpha]_D^{26} - 3.1°$ (c=0.3, CHCl$_3$).

Analysis—Calc'd. for $C_{15}H_{19}NO_3$: C, 68.94;H, 7.33;N, 5.36. Found: C, 69.02;H, 7.35;N, 5.55.

REFERENCE EXAMPLE 23

To a stirred, ice-cooled suspension of (S)-6,7,8,9-tetrahydro-2-(3-hydroxypropyl)-2H-naphtho[2,3-b][1,4]oxazin-3(4H)-one (1.15 g) in a mixture of dichloromethane (40 ml) and triethylamine (0.45 g), was added dropwise methanesulfonyl chloride (1.01 g). The whole was stirred at 0° C. for 1.5 hour, washed with water and dried over magnesium sulfate. The solvent was distilled off and the residue was purified by column chromatography on silica gel (60 g) with ethyl acetate-hexane (3:2, v/v). The resulting crystals were recrystallized from methanol to yield (S)-6,7,8,9-tetrahydro-2-(3-mesyloxypropyl)-2H-naphto[2,3-b][1,4]oxazin-3(4H)-one as colorless needles (1.19 g, 79.7%), m.p. 153°–154° C. $[\alpha]_D^{26} + 4.8°$ (c=0.8, CHCl$_3$).

Analysis—Calc'd. for $C_{16}H_{21}NO_5S$: C, 56.62;H, 6.24;N, 4.13. Found: C, 56.59;H, 6.20;N, 4.14.

REFERENCE EXAMPLE 24

Mesylation of (R)-6,7,8,9-tetrahydro-2-(3-hydroxypropyl)-2H-naphto[2,3-b][1,4]oxazin-3(4H)-one in the same manner as in Reference Example 23 gave (R)-6,7,8,9-tetrahydro-2-(3-mesyloxypropyl)-2H-naphtho[2,3-b][1,4]oxazin-3(4H)-one in 77.8% yield. m.p. 154°–155° C. $[\alpha]_D^{26} - 9.3°$ (c=0.3, CHCl$_3$).

Analysis—Calc'd for $C_{16}H_{21}NO_5S$: C, 56.62;H, 6.24;N, 4.13. Found: C, 56.70;H, 6.20;N, 4.24.

REFERENCE EXAMPLE 25

In a manner similar to that of Reference Example 16, 2-amino-4-methoxyphenol was allowed to react with 2,5-dibromovaleryl chloride, then cyclized to give 2-(3-bromopropyl)-6-methoxy-2H-1,4-benzoxazine-3(4H)-one as crystals. The yield was 56.9%. m.p. 102°–103° C. (recrystallization from ether).

What is claimed is:

1. A compound of the formula:

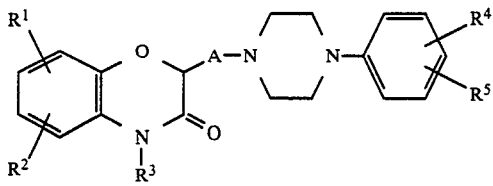

wherein

R¹ and R² independently represent (1) hydrogen, (2) halogen, (3) nitro, (4) lower alkyl which is unsubstituted or is substituted by 1 to 3 substituents selected from halogen, hydroxyl and lower alkoxy, (5) amino which is unsubstituted or is substituted by (a) 1 or 2 β-hydroxyethyl groups, (b) 1 or 2 lower alkyl groups, (c) alkanoyl of 2 to 4 carbon atoms or (d) sulfonyl, (6) hydroxyl which is unsubstituted or is substituted by alkyl of 1 to 6 carbon atoms, phenyl-$C_{1-4}$ alkyl, or alkanoyl of 2 to 4 carbon atoms or (7) lower alkoxycarbonyl, or when R¹ and R² are adjacent to each other, R¹ and R² together may represent a ring represented by $-(CH_2)_m-$ wherein m denotes an integer of 3 to 5 or $-O-(CH_2)_n-O-$ wherein n denotes an integer of 1 to 3, R³ represents hydrogen or lower alkyl, R⁴ and R⁵ independently represent (1) hydrogen, (2) halogen, (3) lower alkyl which is unsubstituted or is substituted by 1 to 3 substituents selected from halogen, hydroxyl and lower alkoxy, or (4) hydroxyl which is unsubstituted or is substituted by alkyl of 1 to 6 carbon atoms, phenyl-$C_{1-4}$ alkyl, alkanoyl of 2 to 4 carbon atoms, or R⁴ and R⁵ combine to form methylenedioxy, and A represents an alkylene group or an acid addition salt thereof.

2. A 1,4-benzoxazine derivative according to claim 1, wherein at least one of R¹ and R² stands for a lower alkoxycarbonyl group.

3. A 1,4-benzoxazine derivative according to claim 1, wherein R¹ and R² combinedly stand for a ring representable by $-(CH_2)_m-$ wherein m denotes an integer of 3 to 5.

4. A 1,4-benzoxazine derivative according to claim 1, wherein R¹ and R² combinedly stand for a ring representable by $-(O-CH_2)_n-O-$ wherein n denotes an integer of 1 to 3.

5. A 1,4-benzoxazine derivative according to claim 1, wherein R³ stands for hydrogen.

6. A 1,4-benzoxazine derivative according to claim 1, wherein at least one of R⁴ and R⁵ stands for hydrogen.

7. A 1,4-benzoxazine derivative according to claim 1, wherein at least one of R⁴ and R⁵ stands for halogen atom.

8. A 1,4-benzoxazine derivative according to claim 1, wherein A stands for ethylene.

9. A 1,4-benzoxazine derivative according to claim 1, wherein A stands for trimethylene.

10. A 1,4-benzoxazine derivative according to claim 1, wherein A stands for trimethylene.

11. A 1,4-benzoxazine derivative according to claim 1, wherein R¹ and R² combinedly stand for a ring representable by $-(CH_2)_m-$ wherein m denotes an integer of 3 to 5 and at least one of R⁴ and R⁵ stands for halogen atom.

12. A 1,4-benzoxazine derivative according to claim 1, wherein at least one of R¹ and R² stands for hydrogen and at least one of R⁴ and R⁵ stands for halogen atom.

13. A 1,4-benzoxazine derivative according to claim 1, wherein R¹ and R² combinedly stand for a ring representable by $-(CH_2)_m-$ wherein m denotes an integer of 3 to 5 and at least one of R⁴ and R⁵ stands for hydrogen.

14. A 1,4-benzoxazine derivative according to claim 1, which is 2-{3-[4-(4-fluorophenyl)-1-piperazinyl]propyl}-6,7,8,9-tetrahydro-2H-naphtho[2,3-b][1,4]-oxazin-3(4H)-one.

15. The 1,4-benzoxazine derivative according to claim 1, which is 2-{3-[4-(3-fluorophenyl)-1-piperazinyl]propyl}-6,7,8,9-tetrahydro-2H-naphtho[2,3-b][1,4]oxazin-3(4H)-one.

16. The 1,4-benzoxazine derivative according to claim 1, which is 2-{3-[4-(2-methoxyphenyl)-1-piperazinyl]propyl}-6,7,8,9-tetrahydro-2H-naphtho]2,3-b][1,4]-oxazin-3(4H)-one.

17. The 1,4-benzoxazine derivative according to claim 1, which is 2-{3-[4-phenyl-1-piperazinyl]propyl}-6,7,8,9-tetrahydro-2H-naphtho[2,3-b][1,4]oxazin-3(4H)-one.

18. A pharmaceutical composition which comprises a pharmaceutically effective amount of a compound according to claim 1 or a pharmacologically acceptable acid addition salt thereof and a pharmacologically acceptable carrier or diluent therefor.

19. A method for the prophylaxis or treatment of hypertension or ischemic disease which comprises administering to a mammal an effective amount of a compound acording to claim 1 or a pharmacologically acceptable acid addition salt thereof.

* * * * *